United States Patent [19]

Webb

[11] 4,333,456

[45] Jun. 8, 1982

[54] SELF-ASPIRATING HYPODERMIC SYRINGE AND SELF-ASPIRATING ASSEMBLY THEREFOR

[75] Inventor: William G. Webb, Rensselaer, N.Y.

[73] Assignee: Sterling Drug Inc., New York, N.Y.

[21] Appl. No.: 232,630

[22] Filed: Feb. 9, 1981

[51] Int. Cl.³ .............................................. A61M 5/22
[52] U.S. Cl. ........................... 128/218 R; 128/218 D
[58] Field of Search ........... 128/218 R, 218 D, 218 P, 128/218 PA, 218 F, 215, 276, 234, 224

[56] References Cited

U.S. PATENT DOCUMENTS

| | | |
|---|---|---|
| 2,904,044 | 9/1959 | Jalar et al. |
| 3,115,135 | 12/1963 | Sarnoff . |
| 3,224,445 | 12/1965 | Melott . |
| 3,295,525 | 1/1967 | Evers et al. |
| 3,340,872 | 9/1967 | Cox . |
| 3,433,223 | 3/1969 | Black . |
| 3,583,399 | 6/1971 | Ritsky . |
| 3,739,780 | 6/1973 | Ogle . |
| 3,797,487 | 3/1974 | Schmidt . |

FOREIGN PATENT DOCUMENTS 1508686 11/1967 France .

*Primary Examiner*—John D. Yasko
*Attorney, Agent, or Firm*—William G. Webb; B. Woodrow Wyatt

[57] ABSTRACT

A hypodermic syringe of the automatic, or self-aspirating, type for use in combination with cartridge ampoules closed at the lower end by a rubber diaphragm pierceable by a double-ended hypodermic needle and closed at the upper end by a slidable rubber piston comprises a combination of a syringe holder unit and a self-aspirating assembly so-adapted to generate aspirating conditions in the ampoule by the slight backward displacement of the rubber piston.

40 Claims, 15 Drawing Figures

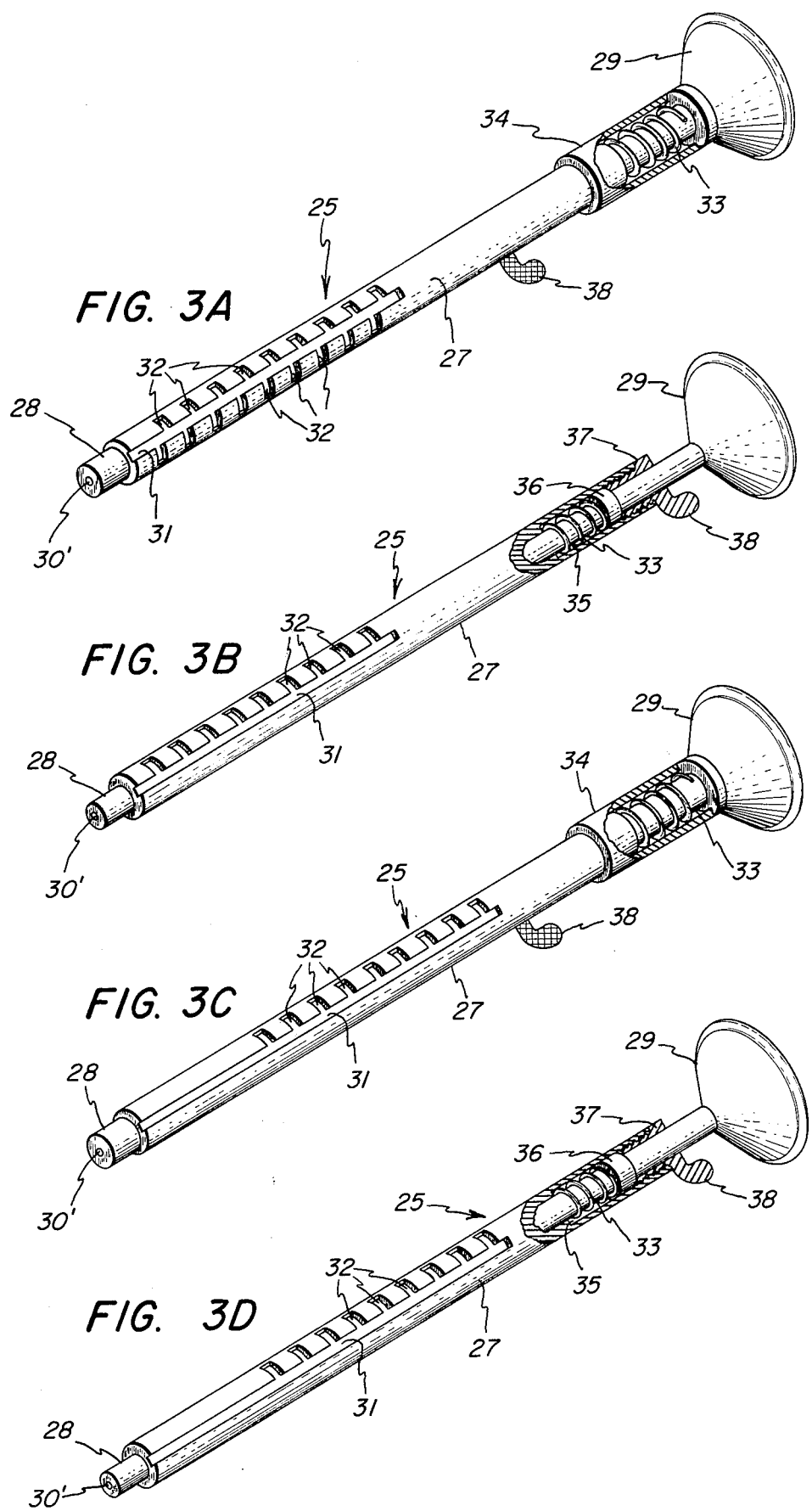

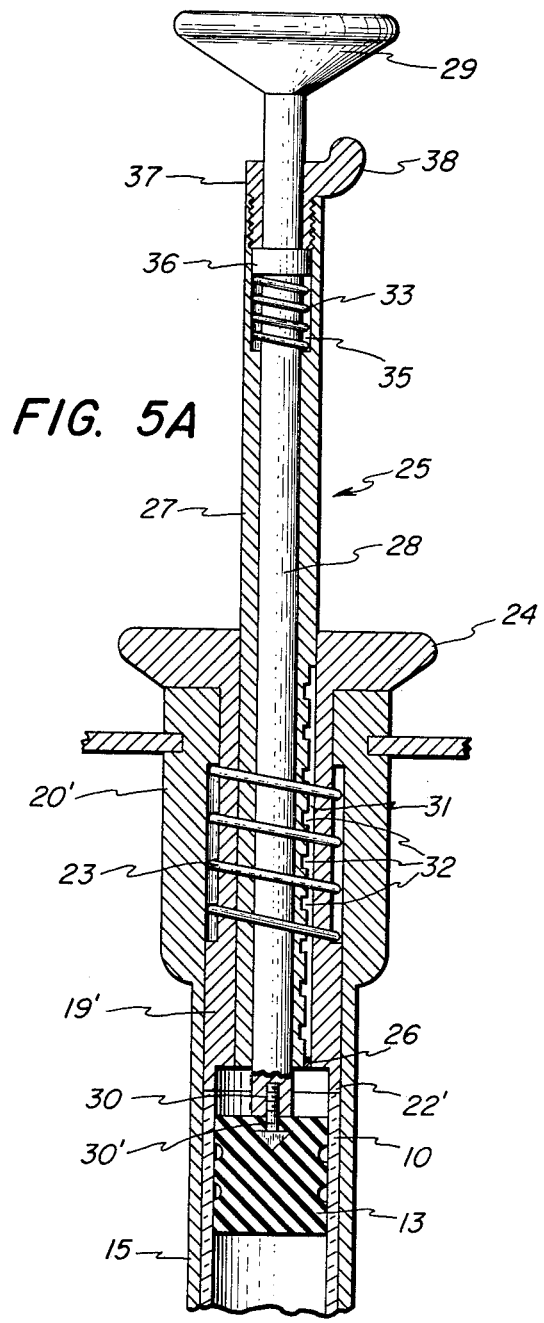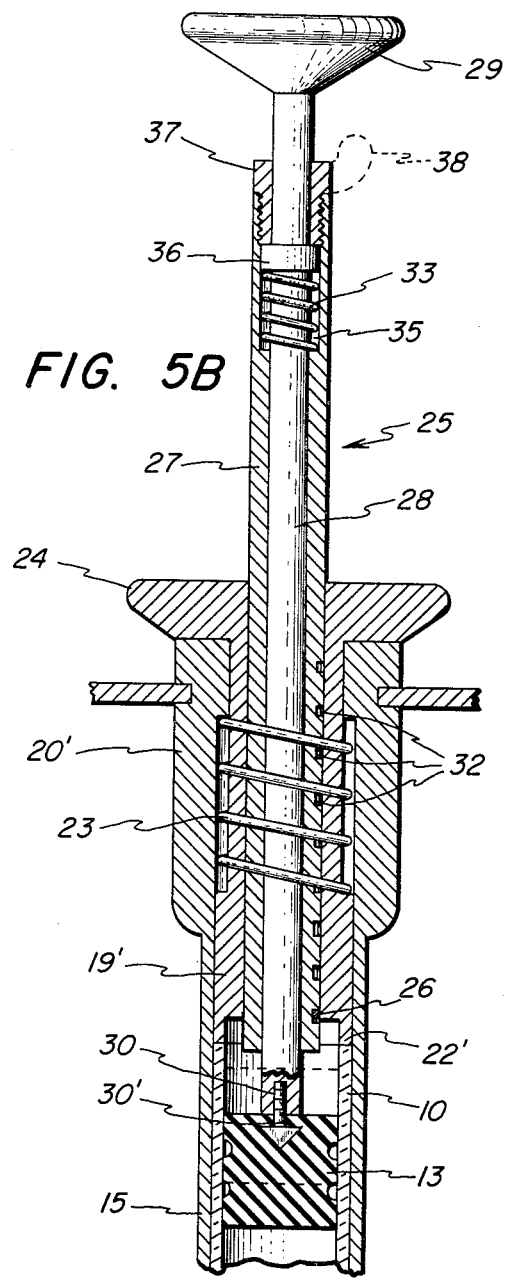

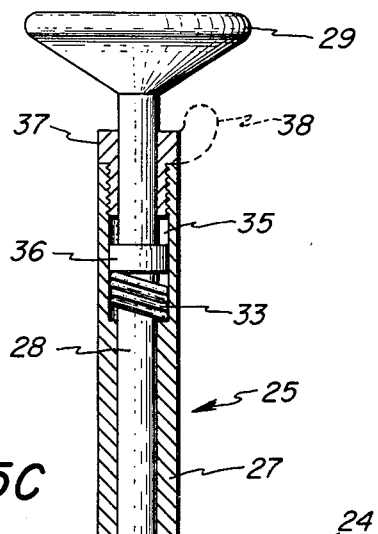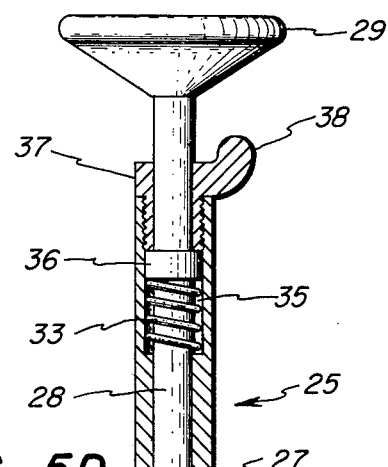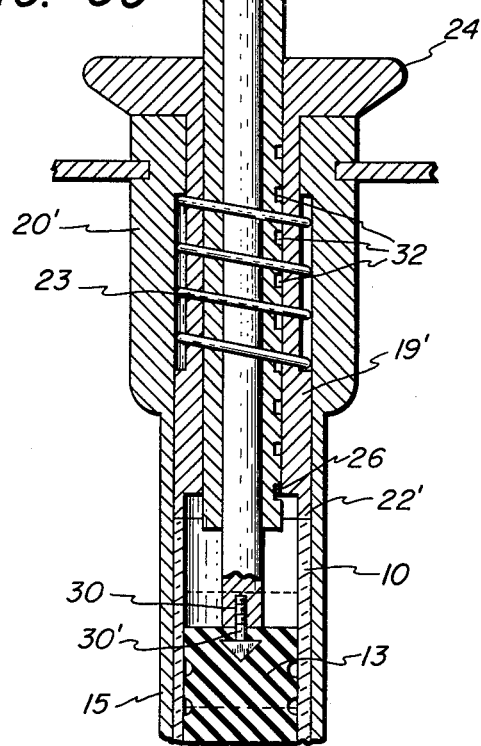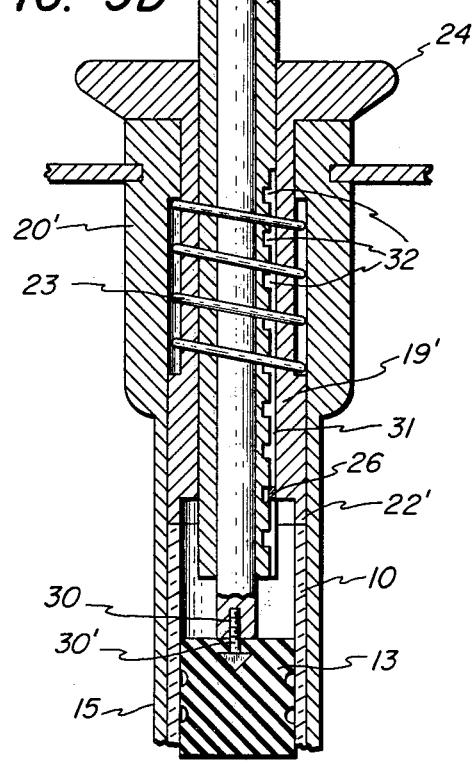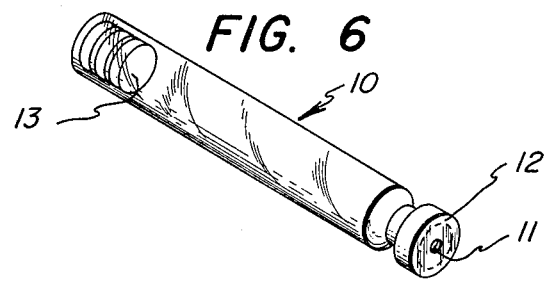

SELF-ASPIRATING HYPODERMIC SYRINGE AND SELF-ASPIRATING ASSEMBLY THEREFOR

BACKGROUND OF THE INVENTION

In medical practice, hypodermic injections are sometimes administered subcutaneously, while others must be given intravenously, depending upon the particular medication to be administered. In either case, it is essential that the practitioner know with certainty, prior to injection of the medication, whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly, or if appropriate the tip can be withdrawn and relocated.

Aspirating syringes useful for the above stated purpose are generally of two types, that is either manually or automatically actuated. It is conventional in both manual as well as automatic aspirating syringes to use cartridge ampoules of the disposable, pre-loaded type, the lower end of which is closed by a flexible rubber diaphragm, which is piercable by one end of a double-ended needle and secured to the ampoule by a crimped-on overcap, the upper end being closed by a piston slidable within the bore of the cartridge ampoule.

Syringes of the automatic aspirating type are often referred to as self-aspirating syringes. The syringes provided by the present invention are of the latter type and are used in conjunction with disposable cartridge ampoules of the type described above.

THE PRIOR ART

Aspiration in syringes of the manual type used with cartridge ampoules is usually effected by slightly withdrawing the syringe plunger rod after it has been connected to the slidable ampoule piston. Connection between the plunger rod and the slidable piston can be effected by a variety of means, such as by a screw-threaded engagement as in Schmidt, U.S. Pat. No. 3,797,487; by an interlocking jaw/coupling button as in Sarnoff, U.S. Pat. No. 3,115,135; or by a barb or "harpoon" on the syringe plunger which pierces and engages the rubber piston as in Jalar et al., U.S. Pat. No. 2,904,044 or Melott, U.S. Pat. No. 3,224,445. Alternatively, the body of the ampoule itself is withdrawn after locking a slidable ampoule piston to a central hollow post in the syringe body, for example by a screw-threaded engagement, as in Ogle, U.S. Pat. No. 3,739,780. Such manually actuatable aspirating syringes, however, have the disadvantage that their proper use depends in very large measure on the degree of skill of the person administering the injection.

Aspiration in syringes of the automatic or self-aspirating type is effected by first inducing a positive pressure in a medicament-containing portion of the syringe, for example in a disposable cartridge ampoule. On release of the force inducing the positive pressure, a corresponding negative pressure in the syringe is generated thus giving rise to the aspirating effect. In Ritsky, U.S. Pat. No. 3,583,399, induction of the positive pressure is achieved by the inward flexing of a rubber diaphragm, which closes the lower end of a medicament-containing ampoule and which is pierceable by the inner end of a double-ended needle, such flexing resulting from impingement of the lower end of the ampoule against a fixed stud surrounding the inner end of the double-ended needle when the ampoule is pressed downwards. Release of the pressure against the ampoule causes return of the diaphragm to its original planar configuration and consequent generation of a slight negative pressure in the ampoule. Self-aspirating syringes of the type described by Ritsky however have the disadvantage that the self-aspirating effect depends greatly on the elasticity of the rubber diaphragm, and the elasticity in turn depends on a number of other variables such as the type, quality and thickness of the rubber and the size of the opening in the end of the ampoule over which the rubber diaphragm is stretched. Thus, syringes equipped with the stud-actuated self-aspirating feature require the use of carefully standardized ampoules.

In Evers et al., U.S. Pat. No. 3,295,525 and Cox, U.S. Pat. No. 3,340,872, induction of the positive pressure in the medicament-containing ampoule is achieved by the action of a flexible portion of the slidable rubber piston which closes the upper end of the ampoule. In these devices, downward pressure on the syringe plunger causes inward distention of the flexible portion of the rubber piston thus producing the desired positive pressure in the ampoule. Release of pressure against the plunger in the Evers and Cox syringes results in return of the flexible portion to its undistended configuration and consequent generation of a slight negative pressure in the ampoule. Self-aspirating syringes of the type described by Evers et al. and Cox suffer from the disadvantage that the rubber pistons, with the flexible portions as an integral part thereof, require special molding and are thus more expensive than conventional rubber pistons.

A rather elaborate method of achieving self-aspiration in a hypodermic syringe unit is that shown by Black U.S. Pat. No. 3,433,223 which describes a gas powered injection system in which self-aspiration is generated by holding the piston of a cartridge ampoule stationary while the ampoule is moved forward, thus in effect producing a backward motion of the piston.

BRIEF SUMMARY OF THE INVENTION

Ideally a self-aspirating hypodermic syringe employing disposable cartridge ampoules should be relatively simple in construction so as to minimize the cost of production; should be relatively simple to operate; should be capable of manipulation with one hand; should be adaptable to multiple self-aspirating actions with each ampoule; should be capable of expelling trapped air from the ampoule prior to insertion of the needle into the injection site and prior to initiation of the self-aspirating action without either precluding self-aspirating action at a later time in the operation sequence of the syringe or otherwise rendering it inoperative; and should be so-constructed that the self-aspirating hypodermic syringe, either in whole or in part, can be marketed either as single-use disposable (i.e. plastic) units or as reusable units marketed as a self-aspirating hypodermic syringe unit for use in combination with the cartridge ampoules.

The self-aspirating syringes provided by the present invention mimic, automatically, the slight rearward piston displacement action of manually operable syringes, thus generating the slight negative pressure in the cartridge ampoule essential for aspiration. The self-aspirating syringes of the present invention therefore obviate the disadvantages inherent in prior art syringes of the manual type, since the aspirating action is generated automatically which requires no special skill on the part of the practitioner. They also obviate the disadvantages of syringes of the automatic (i.e. self-aspirating) type, because aspirating action is achieved independently of the elasticity of the rubber diaphragm of the cartridge ampoule. Moreover they utilize cartridge ampoules with standard rubber pistons. In addition the syringes provided by the invention achieve each of the above-indicated objectives of an ideal self-aspirating syringe.

More specifically, in one aspect the present invention is directed to combinations of (A) syringe holders having a holding means within the head thereof adapted to securely hold within the barrel thereof a medicament containing cartridge ampoule with (B) self-aspirating assemblies slidable within said holding means which comprise a pair of plungers, one within the other, said plungers being biased one against the other, the inner plunger being adapted for positive interengagement with the rubber piston of the cartridge ampoule and the other plunger being adapted for positive, selective and reversible locking with the body of the syringe holder in order to immobilize the outer plunger against axial motion relative to said syringe holder whereby upon alternate exertion of downward pressure and release thereof upon the inner plunger while the outer plunger is locked, the bias of one plunger against the other produces a slight withdrawal of the ampoule piston thereby generating negative pressure within the cartridge ampoule and whereby, when the outer plunger is unlocked, the self-aspirating assemblies are freely slidable within said holding means.

In a second aspect, the invention resides in the self-aspirating assemblies per se as described above which are used in combination with the syringe holders.

BRIEF DESCRIPTION OF THE DRAWINGS

The invention is described hereinbelow with reference to the accompanying drawings wherein:

FIG. 3A is a perspective view in partial longitudinal section of one embodiment of a self-aspirating assembly of the invention which is useable in combination with either of the syringes depicted in FIGS. 1 and 2A;

FIG. 3B is a perspective view in partial longitudinal section of a further embodiment of a self-aspirating assembly of the invention which is usable in combination with either of the syringes depicted in FIGS. 1 and 2A;

FIG. 3C is a perspective view in partial longitudinal section of a further embodiment of a self-aspirating assembly of the invention which is usable in combination with the syringe depicted in FIG. 2B;

FIG. 3D is a perspective view in partial longitudinal section of a further embodiment of a self-aspirating assembly of the invention which is usable in combination with the syringe depicted in FIG. 2B;

FIGS. 5A–5D are enlarged longitudinal section views on line V—V of FIG. 2A showing the method of operation of a self-aspirating assembly of the invention in combination with a hypodermic syringe holder; and FIG. 6 is a perspective view of a cartridge ampoule used with the syringes of the present invention.

DETAILED DESCRIPTION OF THE INVENTION

Figure 1:
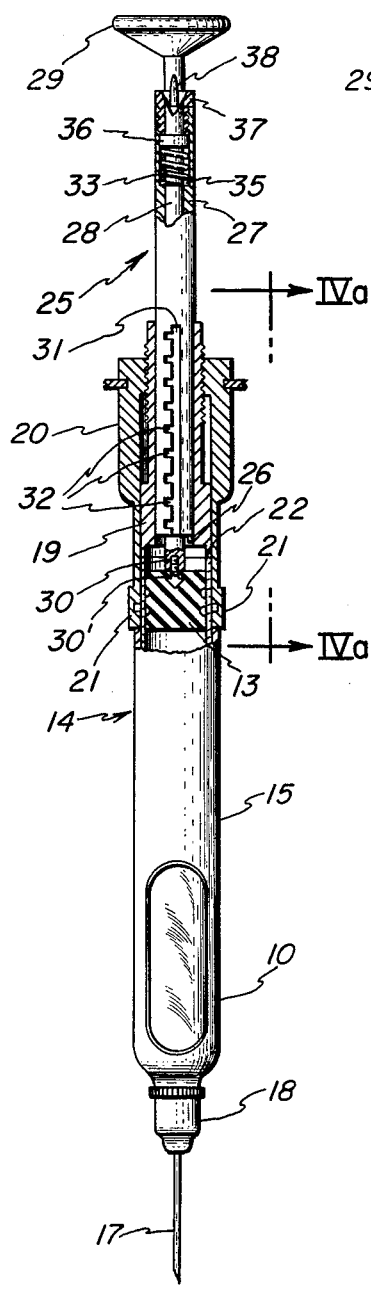
FIG. 1 is an elevational view in partial longitudinal section depicting the combination of a hypodermic syringe of the end-loading type, containing a cartridge ampoule within the barrel thereof, with one embodiment of a self-aspirating assembly of the invention.

The invention will now be described in detail with reference to the foregoing figures where like numerals are used to identify like parts.

In the foregoing discussion and elsewhere in the specification and appended claims, the terms "lower" and "downward" are intended to make reference to the needle end of the hypodermic syringes and associated parts described herein, and conversely the terms "upper" and "upward" are intended to make reference to the head end thereof.

FIG. 6 illustrates a cartridge ampoule, generally indicated by reference numeral 10, of a well-known type which consists of a cylindrical container, usually glass or clear plastic, having a necked-down end and sealed at the necked-down end by a rubber diaphragm 11 which is secured to the ampoule by a crimped on metal collar 12. The other end of the ampoule is closed by a rubber piston 13 which is slidable within the bore of the ampoule.

Figure 2A:
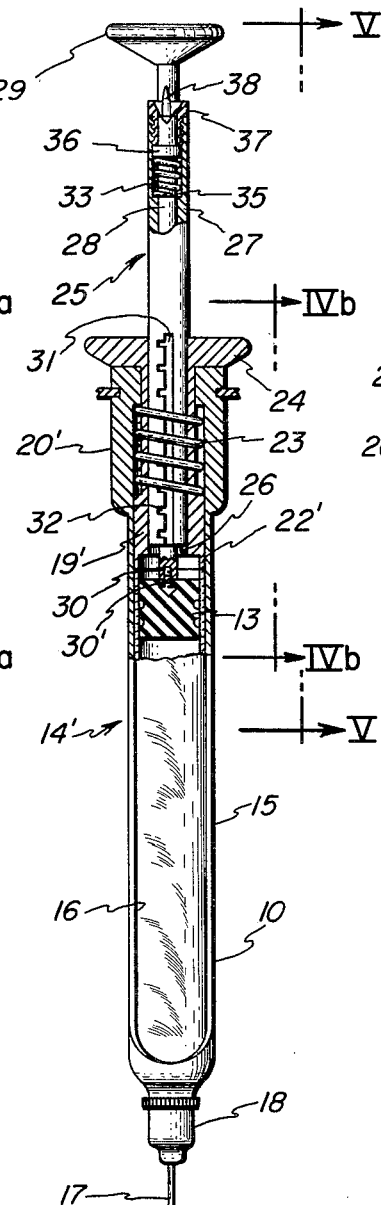
FIG. 2A is an elevational view in partial longitudinal section depicting the combination of a hypodermic syringe of the side-loading type, containing a cartridge ampoule within the barrel thereof, with the same embodiment of a self-aspirating assembly as shown in FIG. 1.
Figure 2B:
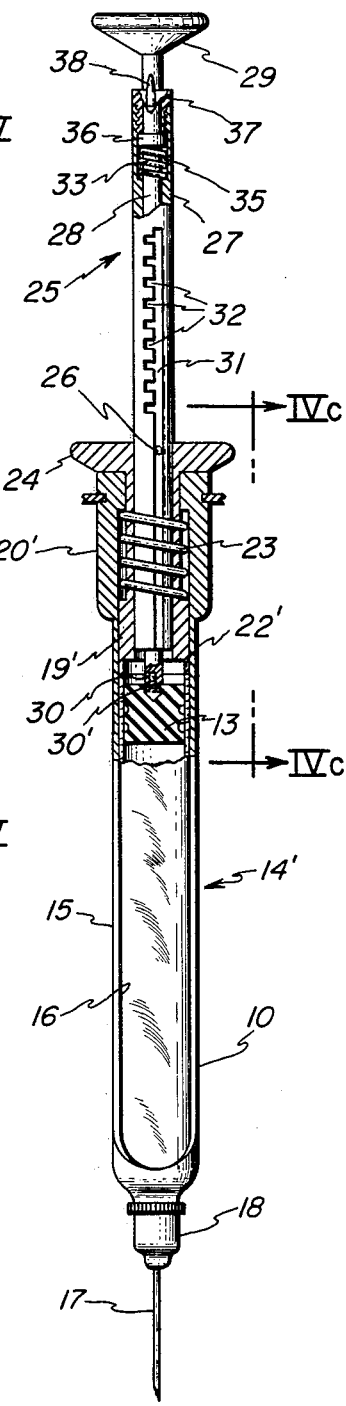
FIG. 2B is an elevational view in partial longitudinal section depicting the combination of a hypodermic syringe of the side-loading type, containing a cartridge ampoule within the barrel thereof, with a further embodiment of a self-aspirating assembly of the invention.

The syringe holders usable in the practice of this invention can be of either the end-loading type, generally indicated by reference numeral 14 in FIG. 1, or of the side-loading type, generally indicated by reference numeral 14' in FIGS. 2A and 2B. These syringes comprise a hollow tubular body or barrel 15 having an elongated window 16 therein for insertion of a cartridge ampoule 10 and fitted at the lower end with a needle 17 and needle hub 18 unit which may be detachably fitted to the syringe holder, for example by means of a screw-threaded mounting. The needle is of the double-ended type so that when a cartridge ampoule 10 is in place within the syringe barrel 15, the inner end of the needle (not shown), pierces the rubber diaphragm 11 so that the needle is in communication with the contents of the ampoule.

In the use of the aspirating syringe units of the present invention, it is necessary that the ampoule 10 be essentially immobilized within the barrel 15 of the syringe holder 14/14'. Accordingly, for this purpose, and with particular reference to FIG. 1, syringes of the end-loading type are equipped with a threaded locking sleeve 19, of generally cylindrical configuration, which is threaded into the syringe head 20. When the threaded locking sleeve is unscrewed, the head 20 can be pivoted about pivot points 21 in order to open the end of the syringe barrel and allow insertion of a cartridge ampoule. Return of the syringe head to its original axial alignment with the barrel and tightening of the screw threaded locking sleeve 19 brings the shoulder 22 of the locking sleeve into locking engagement with the rim of the glass ampoule 10.

In syringes of the side-loading type, such as depicted in FIGS. 2A and 2B, the syringe head 20' is fitted with a locking sleeve 19', the shoulder 22' of which is biased downwards against the rim of the ampoule by compression syringe 23. The syringe holders of the side-loading type here depicted are loaded with a cartridge ampoule by withdrawing the locking sleeve 19' against the bias of compression syringe 23 by means of the flanged head 24 thereof, inserting a cartridge ampoule 10 through the window 16 and releasing the locking sleeve to allow the shoulder 22' to bear against the rim of ampoule 10. The cylindrical locking sleeves 19/19' of the syringe holders of FIGS. 1, 2A and 2B have a bore of sufficient diameter to slidably accept therein a self-aspirating assembly generally indicated by reference numeral 25. The locking sleeves are fitted with a lug 26 located within the bore, which can either be located at the lower end of the locking sleeve of syringes of the end-loading or the side loading types, as depicted in FIGS. 1 and 2A, or at the upper end of the locking sleeve of syringes of the side-loading type as depicted in FIG. 2B.

The purpose of lug 26, which is shown in each of FIGS. 1, 2A and 2B, will now be described with reference to FIGS. 3A–3D, which illustrate the self-aspirating assembly 25 of the invention. This assembly consists of an outer plunger 27 and an inner plunger 28 which is slidable within the bore of the outer plunger. The inner plunger is fitted with a thumb plate 29 at its upper end, and, at its lower end, it is equipped with a means for making positive engagement with the rubber piston 13 of a cartridge ampoule 10. For purposes of illustration only this engagement means is depicted in the drawings herein as a screw threaded post 30 (see FIGS. 1, 2A and 2B), which is threaded into a threaded hole 30' in the lower end of the inner plunger. However it is to be understood that any conventional means known in the art for achieving this purpose is useful in the practice of this invention.

The outer surface of the outer plunger has a longitudinal slot 31 having one or more detents 32 opening to one side or the other of the slot. The width and depth of the slot and the detents are such that the lug 26 is freely slidable within the slot and can be smoothly engaged into the detents when the outer plunger is rotated slightly, for a purpose to be described hereinbelow, when the lug 26 and a particular detent are in lateral alignment with one another. The detents can be arranged in spaced relationship to one another on both sides of the slot as shown in FIG. 3A or, alternatively, they can be arranged on only one side of the slot as depicted in FIGS. 3B–3D.

The inner and outer plungers of the aspirating assembly are biased one against the other by means of a coil spring 33 which can either be mounted within a skirt 34 of thumb plate 29, its lower end bearing against the upper rim of the outer plunger as depicted in FIGS. 3A and 3C, or alternatively the coil spring can be mounted within a cavity 35 in the upper end of the outer plunger as depicted in FIGS. 3B and 3D. In the latter case, the coil spring 33 is biased between the bottom of the cavity 35 in the outer plunger and a shoulder 36 on the inner plunger, the cavity being closed with a screw threaded cap 37.

A thumb tab 38 fixed to the upper end of the outer plunger provides a bearing surface for the thumb of the operator in order to effect slight rotation of the outer plunger for engagement of lug 26 with one of the detents 32 for a purpose to be described below.

The aspirating assemblies 25 of FIGS. 3A and 3B, in which the detents 32 are located near the lower end of the slot 31, are used in combination with a syringe holder in which lug 26 is located near the lower end of locking sleeve 19/19' such as depicted in FIGS. 1 and 2A, while the aspirating assemblies 25 of FIGS. 3C and 3D, in which the detents 32 are placed some distance from the lower end of the outer plunger, are used in combination with syringe holders in which the lug 26 is located near the upper end of the locking sleeve such as depicted in FIG. 2B.

Figure 4A:
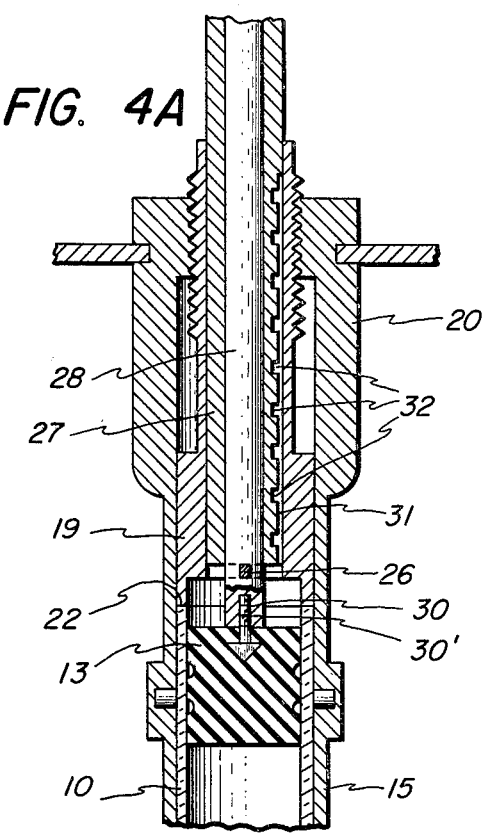
FIG. 4A is an enlarged longitudinal section view on line IVa—IVa of FIG. 1.
Figure 4B:
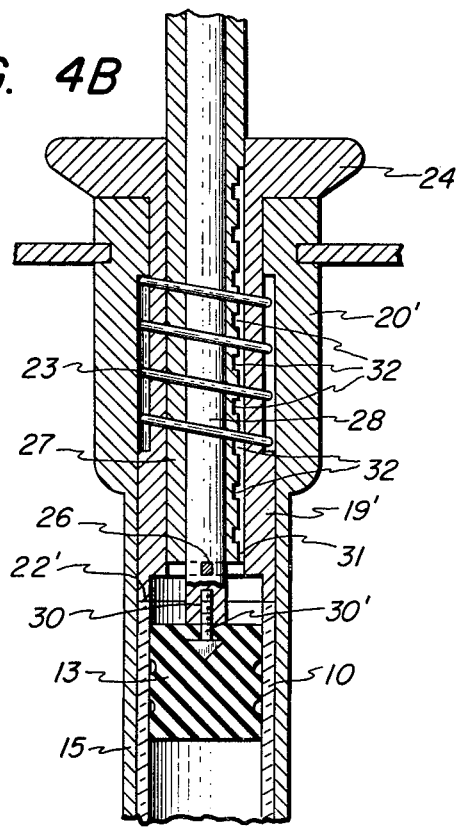
FIG. 4B is an enlarged longitudinal section view on line IVb—IVb of FIG. 2A.
Figure 4C:
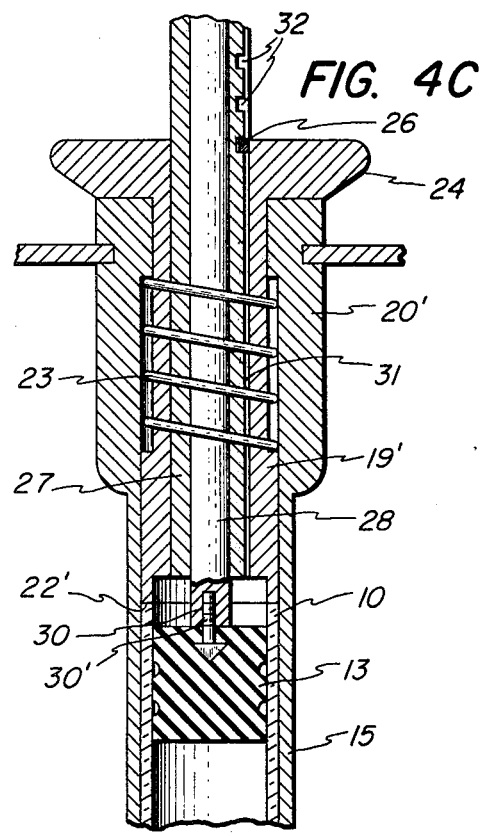
FIG. 4C is an enlarged longitudinal section view on line IVc—IVc of FIG. 2B.

The reason for the difference in the placement of the detents relative to the lower end of the outer plunger will be understood from a consideration of FIGS. 4A–4C which illustrate the combination of the aspirating assembly 25 with a syringe holder 14/14'. The aspirating assembly 25 is inserted in the bore of the locking sleeve 19, the engagement between the inner plunger 28 and rubber piston 13 is effected by interengagement means 30/30'. In the embodiment illustrated by FIGS. 1 and 2A, shown in detail in FIGS. 4A and 4B, respectively, such interengagement can be effected while lug 26 is out of registry with slot 31. However, in the embodiment of FIG. 2B, shown in detail in FIG. 4C, engagement of the inner plunger with the rubber piston by interengagement means 30/30' can only be effected by first aligning the slot 31 with lug 26 and then passing the aspirating assembly through the bore of the locking sleeve in order to effect interengagement of the inner plunger with the rubber piston.

With the aspirating assembly and syringe holder units joined together, the combination is ready for aspirating use. The means by which apsiration is achieved is depicted in FIGS. 5A–5D which illustrate the use of the particular combination shown in FIG. 2A, although it will be appreciated that the combinations shown in FIGS. 1 and 2B operate in a similar fashion to that to be described. Prior to injection of the cartridge ampoule contents into a patient, the practitioner must first expel any air trapped within the ampoule. In the embodiment depicted in FIG. 5A, the outer plunger is therefore first rotated, using the thumb tab 38, until the slot 31 and lug 26 are in alignment. Thereafter, downward pressure on thumb plate 29 forces both the inner and outer plungers downward, displacing rubber piston 13 an equal distance. When all air has been expelled from the ampoule, the outer plunger is rotated slightly using thumb tab 38 so that lug 26 is engaged with one of the detents. At this point in the sequence shown in FIG. 5B, the rubber piston will have moved downwards from its original position indicated by the dotted lines and the needle can then be inserted into the injection site. With the lug engaged in the detent as shown in FIG. 5B, the outer plunger is locked against axial movement in either direction. Thus further downward pressure on the inner plunger will permit displacement of the inner plunger 28 and the rubber piston 13 only to the limit permitted by full compression of coil spring 33 in the cavity 35. The extent of this downward displacement is indicated by the dotted line in FIG. 5C. Upon release of the downward pressure on thumb plate 29, the compressed coil spring 33 produces an upward force on the inner plunger by pressure exerted against shoulder 36, the rubber piston thus being drawn back to its original position indicated by the dotted lines in FIG. 5C.

Assuming that aspiration shows the needle to be properly placed in the patient, injection can be completed by returning the outer plunger to its original orientation with the lug 26 in registry with slot 31 as shown in FIG. 5D. With the outer plunger thus unlocked, the entire inner and outer plunger assembly and rubber piston can be moved downwards either to expel all, or any desired portion of, the ampoule contents. Alternatively, if the practitioner wishes to withdraw the needle from one injection site and inject in a second or more sites, the provision of a multiple number of locking detents permits multiple aspirations, the number of such aspirations being dependent on the number of detents in the outer plunger. As illustrated by the embodiment of FIG. 3A, the number of such detents can be increased by placing them on either side of slot 31 in order to maximize the number of potential selective and reversible locking manipulations of the outer plunger.

It will be appreciated from the above description that the aspirating assemblies and their combination with syringe holders as provided by the present invention possess all the attributes of an ideal aspirating syringe as enumerated above. That is the aspirating assemblies themselves, as well as their combination with syringe holders, are relatively simple in construction, thus minimizing the cost of production; they are relatively simple to operate; they are capable of manipulation with one hand; they are capable of multiple self-aspirating actions with each cartridge ampoule; and they are capable of expelling trapped air from the ampoule either prior to initiation of the self-aspirating action or at any time during the sequence of actions necessary for injection of the ampoule contents without, on the one hand, precluding self-aspirating action at any point in the sequence or, on the other, rendering the self-aspirating action inoperative.

Moreover, the syringe holders and the aspirating assemblies of the invention can be constructed either in whole or in part from metal, to provide reusable units, or from plastic, to provide a disposable syringe holder and/or aspirating assembly.

The syringe holders can also be provided with indicia, for example on the upper face of the flanged head 24 of the embodiments illustrated in FIGS. 2A and 2B in order to indicate when the lug 26 and one of the detents is in alignment to permit locking of the outer plunger prior to aspiration.

It will also be understood that, although the preferred embodiments of the invention have been described above in order to better illustrate the same, alternative structural features can be substituted for elements described herein without either departing from the spirit of the invention or in any way adversely affecting the operability of the same. Thus, for example, a thumb ring conventionally used in manually operating aspirating syringes, although not essential in the operation of the present automatic, self-aspirating system, can nevertheless be used in place of a thumb plate.

Moreover, the use of multiple detents, as illustrated herein, for the purpose of providing multiple aspirating capability is not essential to the operation of the combination, since under certain circumstances a single self-aspirating capability in a syringe would be adequate for effective use of the system. Furthermore, although the first detent 32 is illustrated herein as being located a short distance from the lower end of the outer plunger, in order to provide for the capability of expelling air from the ampoule prior to initiating the first aspirating action, it will be readily appreciated that, by merely lengthening the inner plunger, the first detent can also be located at the extreme lower end of the outer plunger while still retaining the capability of initially expelling air from the ampoule.

In addition, any conventional interengagement means for effecting positive engagement of the inner plunger 28 with the piston 13 can be used instead of the screwthreaded post and hole here depicted. Such other interengagement means include, for example, multiple retractable claws or hooks such as shown in Pontius U.S. No. 2,693,804; a screw threaded engagement into threads molded into the plunger such as disclosed by Lipari U.S. Pat. No. 2,706,984; fixed claws such as described in Breitenbach U.S. Pat. No. 2,789,559; an expandable chuck such as disclosed in Orsten et al. U.S. Pat. No. 2,869,542; resilient gripping fingers such as disclosed in Reznek U.S. Pat. No. 2,895,473; a barbed point or "harpoon" such as disclosed in Jalar U.S. Pat. No. 2,904,044; or a bayonet connection such as disclosed in Hart U.S. Pat. No. 2,986,141.

Having thus described the invention and the advantages thereof, it is considered that the invention is to be broadly construed and limited only by the character of the following claims.

I claim:

1. A self-aspirating hypodermic syringe of the type used in combination with a cartridge ampoule which is sealed at its upper end by a slidable piston and at its lower end by a pierceable membrane and which contains an injectable fluid therein, the syringe having a double ended needle attached thereto for communication with the cartridge ampoule contents via the pierceable membrane, said syringe comprising in combination:

(A) a syringe holder comprising a head, a barrel attached thereto for receiving said cartridge ampoule and provided at its lower end with a double ended needle, and a generally cylindrical holding means within said head which is adapted to securely hold said cartridge ampoule within said barrel; and (B) a self-aspirating assembly slidable within the bore of said holding means comprising a pair of plungers, one slidable within the other, said plungers being biased one against the other, the inner plunger being adapted for positive interengagement with said slidable piston of said cartridge ampoule and the outer plunger being adapted for positive, selective and reversible locking with said holding means thereby to immobilize said outer plunger against axial movement relative to said syringe holder and cartridge ampoule, whereby upon alternate exertion of downward pressure upon said inner plunger while said outer plunger is locked and release of said downward pressure, the said bias of said inner plunger against said outer plunger creates aspirating conditions within said cartridge ampoule and whereby upon exertion of downward pressure upon said inner plunger while said outer plunger is unlocked, said inner and outer plungers are freely slidable within the bore of said holding means.

2. A self-aspirating hypodermic syringe of the type used in combination with a cartridge ampoule which is sealed at its upper end by a slidable piston and at its lower end by a pierceable membrane and which contains an injectable fluid therein, the syringe having a double ended needle attached thereto, the inner end of which extends axially into the barrel of the syringe for communication with the cartridge ampoule contents via the pierceable membrane, said syringe comprising in combination:

(A) a syringe holder comprising a head, a barrel attached thereto for receiving said cartridge ampoule and provided at its lower end with a double ended needle, and a generally cyclindrical holding means within said head which is adapted for securely holding said cartridge ampoule within said barrel; and (B) a self-aspirating assembly slidable within said holding means comprising a pair of plungers, one slidable within the other and having means for biasing said inner and outer plungers one against the other, said inner plunger being adapted for positive interengagement with said slidable piston of said cartridge ampoule, said combination having means for positive, selective and reversible locking of said outer plunger within the head of said syringe holder thereby to immobilize said outer plunger against axial movement relative to said syringe holder, whereby upon alternate exertion of downward pressure upon said inner plunger while said outer plunger is locked and release of said downward pressure, aspirating conditions are created within said cartridge ampoule and whereby upon exertion of downward pressure upon said inner plunger while said outer plunger is unlocked, aspirating conditions are absent, and the contents of said cartridge ampoule are expellable therefrom.

3. The combination according to claim 2 wherein said syringe holder is adapted for side-loading of said cartridge ampoule.

4. The combination according to claim 2 wherein said syringe holder is adapted for end-loading of said cartridge ampoule.

5. The combination according to claim 3 wherein said holding means comprises a spring biased locking sleeve.

6. The combination according to claim 4 wherein said holding means comprises a screw-threaded locking sleeve.

7. The combination according to claim 5 wherein the means biasing the inner and outer plungers against one another comprises a coil spring.

8. The combination according to claim 6 wherein the means biasing the inner and outer plungers against one another comprises a coil spring.

9. The combination according to claim 7 wherein said locking means comprises a lug affixed within the bore of said locking sleeve for cooperative engagement with a slot and associated detent means on the outer surface of said outer plunger.

10. The combination according to claim 8 wherein said locking means comprises a lug affixed within the bore of said locking sleeve for cooperative engagement with a slot and associated detent means on the outer surface of said outer plunger.

11. The combination according to claim 9 wherein said lug is positioned near the lower end of said locking sleeve.

12. The combination according to claim 9 wherein said lug is positioned near the upper end of said locking sleeve.

13. The combination according to claim 10 wherein said lug is positioned near the lower end of said locking sleeve.

14. The combination according to claim 11 wherein said detent means comprises multiple detents.

15. The combination according to claim 12 wherein said detent means comprises multiple detents.

16. The combination according to claim 13 wherein said detent means comprises multiple detents.

17. The combination according to claim 14 wherein said inner plunger is provided at the upper end thereof with a thumb plate and dependent skirt and wherein the coil spring biasing means between the inner and outer plungers is contained within said skirt.

18. The combination according to claim 14 wherein said outer plunger is provided with a cavity at the upper end thereof for receiving a shoulder near the upper end of said inner plunger and wherein the coil spring biasing means between the inner and outer plungers is contained within said cavity.

19. The combination according to claim 15 wherein said inner plunger is provided at the upper end thereof with a thumb plate and dependent skirt and wherein the coil spring biasing means between the inner and outer plungers is contained within said skirt.

20. The combination according to claim 15 wherein said outer plunger is provided with a cavity at the upper end thereof for receiving a shoulder near the upper end of said inner plunger and wherein the coil spring biasing means between the inner and outer plungers is contained within said cavity.

21. The combination according to claim 16 wherein said inner plunger is provided at the upper end thereof with a thumb plate and dependent skirt and wherein the coil spring biasing means between the inner and outer plungers is contained within said skirt.

22. The combination according to claim 16 wherein said outer plunger is provided with a cavity at the upper end thereof for receiving a shoulder near the upper end of said inner plunger and wherein the coil spring biasing means between the inner and outer plungers is contained within said cavity.

23. The combination according to claim 17 wherein said needle and needle hub unit is threadably removeable from the lower end of said barrel.

24. The combination according to claim 18 wherein said double ended needle is associated with a threadably removeable hub.

25. The combination according to claim 19 wherein said double ended needle is associated with a threadably removeable hub.

26. The combination according to claim 20 wherein said double ended needle is associated with a threadably removeable hub.

27. The combination according to claim 21 wherein said double ended needle is associated with a threadably removeable hub.

28. The combination according to claim 22 wherein said double ended needle is associated with a threadably removeable hub.

29. A self-aspirating assembly for use in combination with a hypodermic syringe holder having a head, a barrel attached thereto for receiving a cartridge ampoule closed at its inner end by a slidable piston, and a generally cylindrical holding means within said head, said self-aspirating assembly comprising a pair of plungers, one within the other, said plungers being biased one against the other, the inner plunger being adapted for positive interengagement with the slidable piston of said cartridge ampoule held within said syringe holder and the outer plunger being adapted for positive, selective and reversible locking with said holding means thereby to immobilize said outer plunger against axial movement relative to said syringe holder and cartridge ampoule.

30. A self-aspirating assembly for use in combination with a hypodermic syringe holder having a head, a barrel attached thereto for receiving a cartridge ampoule closed at its inner end by a slidable piston, and a generally cylindrical holding means within said head, said self-aspirating assembly comprising a pair of plungers, one slidable within the other and having means for biasing said inner and outer plungers one against the other, said inner plunger being adapted for positive interengagement with the slidable piston of said cartridge ampoule held within said syringe holder and said outer plunger having means for positive, selective and reversible locking of said outer plunger within the head of said syringe holder thereby to immobilize said outer plunger against axial movement relative to said syringe holder.

31. The assembly according to claim 30 wherein said biasing means between the inner and outer plungers comprises a coil spring.

32. The assembly according to claim 31 wherein said locking means comprises a slot and detent means on the outer surface of the outer plunger for engagement with a lug affixed within the bore of said holding means.

33. The assembly according to claim 32 wherein said detent means is positioned so as to be engageable with said lug when located near the lower end of said holding means.

34. The assembly according to claim 32 wherein said detent means is positioned so as to be engageable with said lug when located near the upper end of said holding means.

35. The assembly according to claim 33 wherein said detent means comprises multiple detents.

36. The assembly according to claim 34 wherein said detent means comprises multiple detents.

37. The assembly according to claim 35 wherein said inner plunger is provided at the upper end thereof with a thumb plate and dependent skirt and wherein the coil spring biasing means between the inner and outer plungers is contained with said skirt.

38. The assembly according to claim 35 wherein said outer plunger is provided with a cavity at the upper end thereof for receiving a shoulder near the upper end of said inner plunger and wherein the coil spring biasing means between the inner and outer plungers is contained within said cavity.

39. The assembly according to claim 36 wherein said inner plunger is provided at the upper end thereof with a thumb plate and dependent skirt and wherein the coil spring biasing means between the inner and outer plungers is contained with said skirt.

40. The assembly according to claim 36 wherein said outer plunger is provided with a cavity at the upper end thereof for receiving a shoulder near the upper end of said inner plunger and wherein the coil spring biasing means between the inner and outer plungers is contained within said cavity.

* * * * *